United States Patent [19]

Peleg et al.

[11] Patent Number: 4,795,635
[45] Date of Patent: Jan. 3, 1989

[54] VACCINE SYSTEM

[76] Inventors: Ben-Ami Peleg, 3 Harimon Street, Rehovot; Karol Hornstein, 2 Hildesheimer Street, Tel-Aviv; Hagay Yadin, 18 Sderot Chen, Rehovot, all of Israel

[21] Appl. No.: 102,794

[22] Filed: Sep. 23, 1987

Related U.S. Application Data

[63] Continuation of Ser. No. 827,622, Feb. 10, 1986, abandoned.

[30] Foreign Application Priority Data

Feb. 10, 1985 [IL] Israel ......................................... 74289

[51] Int. Cl.$^4$ ............................................. A61K 39/17
[52] U.S. Cl. ...................................................... 424/89
[58] Field of Search .............................. 424/88, 89, 92

[56] References Cited

U.S. PATENT DOCUMENTS 4,650,677  3/1987  Roerink ................................. 424/89

FOREIGN PATENT DOCUMENTS 0073856  3/1983  European Pat. Off. .
0129823  1/1985  European Pat. Off. .

*Primary Examiner*—Shep K. Rose
*Attorney, Agent, or Firm*—Fleit, Jacobson, Cohn & Price

[57] ABSTRACT

There is provided a vaccine system which is of use in the vaccination of mammal, avian and fish species by injection. The system comprises a non-virulent vaccine of viral, bacterial, mycoplasmal, chlamydial or fungal microorganisms, and mixtures of any of these, on the one hand, and a suitable adjuvant of the water-in-oil type; these being admixed with each other just before administration of the vaccine by injection.

1 Claim, No Drawings

VACCINE SYSTEM

This application is a continuation of application Ser. No. 827,622, filed Feb. 10, 1986, now abandoned.

BACKGROUND OF THE INVENTION

This intensive methods of raising animals for food (meat, eggs & milk) under modern agricultural conditions make it imperative to immunize actively against a wide range of diseases.

Avian and mammalian species are susceptible to many disease causing organisms which endanger any farm, be it the most remote & isolated. Such devastating diseases as Newcastle disease, Fowl Pox, Infectious Laryngotracheitis, Infectious Bronchitis in poultry & Infectious Bovine Rhinotraceitis, Bovine Viral Diarrhea, clostridial infections in cattle & sheet are only a few.

Since Louis Pasteu's vaccines against Fowl Cholera and Rabies, numerous vaccines have been developed and successfully applied under various conditions all over the globe. These different types can be divided into two major categories: Live Vaccines & Inactivated or Killed Vaccines. Live Vaccines utilize living cultures of attenuated or naturally mild strains of the microorganism, while inactivated vaccines use the natural or another form of the disease-causing agent in a biologically inactive state.

There are several basic differences between these two categories of immunizing preparations. Live Vaccines have the advantages of:

Mass application to large populations under some circumstances (via drinking water, aerosol spray, etc.)

A relatively small quantity of the immunizing agent is necessary to illicit immunity, because the live organism multiplies in the body of the vaccinated animals.

Live Vaccines are usually more economical and cheaper to apply.

They require relatively small space under cold storage.

On the other hand, live vaccines have an important disadvantage:

The immunity which results from vaccination of animal with live vaccines is often very short lived, necessitating repeated additional vaccinations.

Inactivated vaccines are different from live ones. Their advantages are:

The safety of using an inactivated (killed) microorganism is obvious, and constitutes the major advantage over live vaccines.

Inactivated vaccines are often coupled with an Adjuvant, a chemical or biological entity which serves to enhance the immunizing capability of the inactivated microorganism. As combined antigen and adjuvant the inactivated vaccine becomes potent and effective. Such vaccines have a longer lasting effect than live vaccines.

Their disadvantages are also of importance:

Inactivated vaccines are more expensive to produce because they have to contain a larger mass of the antigen in order to ellicit a good immune response;

Some inactivation methods alter the surface antigen configuration and thus the specificity of the vaccine is reduced.

Inactivated vaccines must be applied by individual injection of every animal, and cannot be applied by mass application methods.

They occupy sizeable volumes and weights which require cold storage.

They often cause reactions at the site of injection; in the case of oil adjuvants, these may become granulomatous.

Adjuvants, as mentioned above, have become important components of inactivated vaccines. There exists biological adjuvants, such as bacterial endotoxins; pneumococcus capsular extracts of Lipopoly-saccharides (LPS) nature; whole Mycobacterium organisms and subunit components of mycobacterial cell walls. Irritants such as saponin have served as adjuvants in various vaccines. Surface-active chemical entities have been tried, such as detergents, polyols, polyanionics; and also polynucleotides have been used. Adjuvants have been used which produce physical configurations to "present" the antigen in a protected form and slow release mechanism such as Liposomes; or in a different concept—the antigen is adsorbed onto molecules of Aluminum hydroxide gel.

One of the most widely used adjuvants is the water-in-oil (w/o) emulsion, of the Freund's Incomplete Adjuvant (F.I.A.) type. This system includes and aqueous (or water) phase in which the antigen is dissolved or suspended; and oil phase in which the water phase is suspended as small droplets; and interface between the water & oil phases, usually lined by emulsifiers which stabilize the emulsion.

W/O emulsified vaccines are very potent and effective immunizing agents. The exact mechanism of immune potentiation is not very well proven. It is believed to be either an antigen-presentation mechanism; a depot of antigen which remains for extended periods of time at the injection site; a substance which attracts large numbers of macrophages which then enhance the immune response, or all these whichever is the real mechanism the net effect is that w/o emulsified vaccines are very good immunogens. Animals so vaccinated usually respond with a high level of immunity-both humoral & cellular; the immunity is very long lasting, often extending over a year or two; the levels of immunity obtained in animal populations are usually very uniform.

Under some circumstances, and in order to reduce the reaction at injection site a double emulsion is used; the water-in-oil-in-water (w/o/w) emulsion. This type of vaccine is very similar to the w/o type.

Best results of vaccination with w/o type vaccines are obtained in poultry for example, when a live & inactivated vaccine are combined. This can be done simultaneously, on one day old chicks, turkey poults, etc. vaccinated against Newcastle disease at the hatchery. Chicks are vaccinated by spray, by aerosol, or by occular or nasal drop methods with a live Newcastle disease vaccine such as the Hitchner B1 strain & at the same time they are injected with a small volume (usually 0.1–0.2 ml) of inactivated w/o emulsified Newcastle disease vaccine.

This combined vaccination results in an immunization which overcomes the maternal (passive) immunity of the chicks, which ordinarily interferes with active immunization of young chicks. (D. Warden, I. G. S. Furminger & W. W. Robertson, 1975; W. W. Robertson, et al 1976).

Later on it was realized that "priming" an animal with a live vaccine and "boosting" the immunity with an inactivated w/o vaccine later results in excellent & lasting immunity. It has become standard procedure with poultry breeders to vaccinate growing pullets once or more with live vaccines and then follow up with w/o emulsified killed vaccine before point-of-lay.

Thus breeding & laying hens are immunized to obtain a high and uniform level of immunity which lasts throughout the laying period (some 10 to 12 months) or longer. This is practiced in the cases of Newcastle Disease, Infectious Bursal Disease ("Gumboro Disease"), Infectious Bronchitis, Viral Arthritis, etc. In all these cases, the live vaccines are composed of attenuated or naturally occurring mild strains of the disease causing agents, which are harmless or very mild in the side reactions which occur following their use.

SUMMARY OF THE INVENTION

There is provided a vaccine system comprising the components of both live & w/o or w/o/w emulsified inactivated vaccines. There is used a live vaccine to be combined just prior to use with a w/o emulsion which is sterile, and does not contain any antigen at all. The w/o emulsion is composed of an aqueous phase which may be made up of water, saline, a buffer (such as phosphate buffered saline) or another type of inocuous solution; of an oil phase which is composed of a mineral oil (such as Drakeol or another oil made up of various lengths of carbohydrate chains) or a vegetable oil (such as sesame, peanut, corn oils, etc.); and emulsifiers for the aqueous phase such as Tween 40, 60, 80 etc. (POE sorbitan monopalmitate, monosterarate, monooleate, etc.) and for the oilphase such as Arlacel A, Arlacel 80, etc. (Sorbitan monostearate, sorbitan monooleate, mannide monooleate, etc.).

The live vaccine is usually presented as a live culture of virus, bacterium or another microorganism, usually in a stabilized form, such as dry freeze-dried (lyophilized) "cake" or powder. The live vaccine is reconstituted just prior to use with a small volume of water.

The reconstituted live vaccine is them poured into the w/o emulsion and thoroughly mixed by shaking. This procedure causes the live vaccine to disperse into the w/o emulsion and it finds its way into the aqueous phase.

This mixture of live vaccine & w/o emulsion is then injected into the animal. The result is that an intense and effective immune reaction is set up in the vaccinated animal which combines the advantages of both vaccine types. The immunity is very high, as expressed in circulating antibody levels; it is uniform in the vaccinated population; and it is long lasting. The advantages of such vaccine systems are:

A live vaccine is used, which contains a relatively small quantity of antigen, which is a cost saving factor, as live vaccines are much cheaper than inactivated ones. The live vaccine multiplies in the vaccinated animal's body.

The live vaccine is packaged in very small vials which require small cold storage space, while the w/o emulsion component is very stable and does not require cold storage. It has a long shelf life and can be kept under any reasonable storage conditions.

The resultant immunity generally surpasses the results obtained from a single live vaccine application.

It is unnecessary to combine two vaccination applications;

It actually combines the "priming" and the "booster" vaccinations into one step, so as to make the whole process time and labor saving.

EXAMPLES

EXAMPLE NO. 1

32 day-old light cross chickens (white Leghorn×Rhode Island Red) previously not vaccinated were used. Groups of 20 birds each were treated as follows: 1 group was vaccinated with a live Newcastle disease vaccine (V.H. strain) given as subcutaneous injection; 1 group was similarly vaccinated with the LaSota strain; 1 group was vaccinated by subcutaneous injection with the V.H. strain mixed with a w/o emulsion, at 0.5 ml volume for each chicken; 1 group served as unvaccinated controls. Table 1 summarizes results of Hemagglutination Inhibition (HI) titres as the geometric mean at Log 2, at various intervals post vaccination. The w/o emulsion contained saline+Tween 80 (water phase) & Drakeol+Arlacel A as the oil phase. (as described by D. Lombardi 1966; Z. Zakay-Rones & R. Levy 1973).

TABLE No. 1

| Vaccination | HI Results after vaccination on day | | | | | | |
|---|---|---|---|---|---|---|---|
| | 0 | 7 | 20 | 30 | 41 | 51 | 62 |
| VH + w/o | 1.0 | 1.0 | 3.0 | 4.2 | 4.1 | 3.9 | 3.9 |
| VH only | 1.0 | 1.0 | 1.35 | 1.85 | 1.8 | 1.6 | 1.8 |
| LaSota + w/o | 1.0 | 1.0 | 2.6 | 4.0 | 4.6 | 4.0 | 4.0 |
| LaSota only | 1.0 | 1.9 | 2.0 | 2.0 | 2.0 | 1.8 | 2.4 |
| Unvaccinated controls | 1.0 | 1.0 | 1.0 | 1.0 | 1.0 | 1.0 | 1.2 |

From these results it can easily be observed that susceptible chickens are well protected by the mixed live-w/o emulsion vaccine, as compared to unvaccinated controls and to those vaccinated with the live vaccine only.

EXAMPLE NO. 2

63 day-old chickens were used in this experiment. Groups of 15 birds each were treated. 1 group was vaccinated by the wing-web route using a vaccination needle, with Fowl Pox vaccine-live virus of commercial type produce, utilizing the appropriate glycerinated saline diluent. 1 group was vaccinated by subcutaneous injection of mixture of the same live fowl pox vaccine diluted in distilled water and mixed thoroughly into a w/o emulsion as was used in experiment No. 1. 1 group was unvaccinated and served as controls. Table 2 summarized the results of the experiment. Assessment of immunity was carried out be challenge of the chickens by the cutaneous route with a fowl pox virus and reading the site of cutaneous challenge 6 to 10 days later. Positive results (pock or crust lesions) indicated lack of immunity at time of challenge.

TABLE No. 2

| Vaccination | Challenge results | 21 days post vaccination |
|---|---|---|
| Fowl Pox alone | 0/15* | |
| Fowl Pox in w/o | 0/15 | |
| Controls | 15/15 | |

*No. of birds positive after challenge out of 15 challenged.

These results demonstrate that although fowl pox vaccine is usually successful in conferring immunity by transcutaneous vaccination, the live vaccine mixed into the w/o emulsion immunizes the chickens against challenge with the virus.

EXAMPLE 3

60 chickens, at 63 days of age were used. 15 served as controls and 45 were vaccinated with an w/o emulsion as described under Ex. No. 1 and into which were mixed 2 live vaccines—LaSota strain of live Newcastle disease virus and attenuated fowl pox virus. The double live vaccine w/o mixture was subcutaneously injected into the 45 birds at a 0.5 ml volume in the neck region. 21 days later the birds were challenged with fowl pox virus as described under Ex. No. 2 HI tests were carried out on blood samples collected from these birds to assess immunity against Newcastle disease. Table 3 summarizes the results.

TABLE No. 3

| Vaccination | Fowl Pox Challenge | Newcastle HI results | |
|---|---|---|---|
| | | 0 days | 21 days |
| Fowl Pox + Newcastle in w/o | 2/45 | 1.0 | 4.0 |
| Controls | 15/15 | 1.1 | 1.0 |

The results of this run indicate that the new system is effective with multiple live microorganisms as well as with single entities.

The indications of the above are pointing to the direction that the use of live vaccines admixed into a previously prepared w/o emulsion just prior to injection into animals is an effective, simple and economically advantageous method for immunizing animals. The system enhances the immunizing capabilities of live vaccines with results similar to those obtained with inactivated oil emulsion vaccines, but with cost & storage saving advantages which are very considerable.

Various adjuvant-antigen systems do work on a similar basis. The exact mechanism by which these systems operate are not completely understood to this very date. The admixture of live vaccines with a w/o emulsion is not the only combination applicable. Similar results can be achieved when other adjuvants are used.

Furthermore, knowing that different antigenic entities operate on identical immune system components, such as macrophages, helper T cells, precursor T cells, B cells; as well as interleukins and other factors (proliferating or suppressor ones), it is evident that many antigens will illicit the same type of enhanced response when admixed with an adjuvant system. Fowl-pox virus and Newcastle disease virus, many other viruses, bacteria, and also mycoplasmata, chlamydia and fungi behave similarly.

In a similar manner it is possible to prepare vaccination system comprising various types of bacteria and emulsions as set out above.

*Pasteurella multocida* live attenuated, (strain Cleson University-CU Strain or M-3 G); *Bacillus anthracis* (Stern's Spare vaccine), *Brucella abortus* (Strain Buck 19), *Brucella melitensis* (Strain Rev-1); of *Mycoplasma Gallisepticum*, and to obtain effective immunity.

Experiments were carried out in order to compare the efficiency of water-in-oil versus oil-in-water emulsion when used in compositions for the vaccination.

20 chicken of the type used in Example 1 were vaccinated against Newcastle disease (the strain of Example 1), as set out in this Example.

In one experiment there was used an oil-in-water emulsion, in the other a water-in-oil emulsion. Both groups of birds were vaccinated with vaccines prepared by mixing a short time before the injection.

The results were evaluated after 14 days by establishing the concentration in the blood of antibodies against Newcastle by the HI (Hemagglutination Inhibition) test. It was found that group 1 (oil in water emulsion) gave a level of $Log_2 1.9$, whereas Group 2 (water in oil) gave a level of $Log_2 4.0$, thus demonstrating the substantial superiority of the water-in-oil emulsion for such vaccinations.

The test was carried out after 14 days, and proves the high titer attained by compositions of the invention, versus unsatisfactory results of oil in water emulsion.

Similar results can be attained by the admixture of other types of adjuvant with a non-virulent vaccine a short period of time prior to vaccination. Amongst suitable adjuvants there may be mentioned certain detergents, polymers, polyols and liposomes, and whenever the term "adjuvant" is used herein, this is intended to encompass also this type of adjuvants.

We claim:

1. In the art of vaccinating fowl against Newcastle Disease with emulsion adjuvanted live Newcastle Disease virus vaccines the improvement consisting of the step of vaccinating the fowl with live Newcastle Disease virus vaccines in a water-in-oil emulsion prepared by mixing a short time before the injection and injecting the mixture within a short period of time after such admixture.

* * * * *